(12) United States Patent
Peng et al.

(10) Patent No.: US 7,663,002 B2
(45) Date of Patent: Feb. 16, 2010

(54) HYDROFORMYLATION PROCESS AND PRODUCT SEPARATION WITH IMPROVED RECOVERY OF RHODIUM

(75) Inventors: Wei-Jun Peng, Midland, MI (US); Kurt D. Olson, Freeland, MI (US); Donald L. Morrison, Fort Collins, CO (US); Brian M. Roesch, Middletown, DE (US); Donald L. Bunning, South Charleston, WV (US); Jeffrey G. Hippler, South Charleston, WV (US); Vincent J. Stricker, Charleston, WV (US)

(73) Assignee: Dow Global Technologies, Inc., Midland, MI (US)

( * ) Notice: Subject to any disclaimer, the term of this patent is extended or adjusted under 35 U.S.C. 154(b) by 0 days.

(21) Appl. No.: 12/299,853

(22) PCT Filed: Apr. 17, 2007

(86) PCT No.: PCT/US2007/009452

§ 371 (c)(1),
(2), (4) Date: Nov. 6, 2008

(87) PCT Pub. No.: WO2007/133379

PCT Pub. Date: Nov. 22, 2007

(65) Prior Publication Data

US 2009/0118548 A1    May 7, 2009

Related U.S. Application Data

(60) Provisional application No. 60/800,555, filed on May 15, 2006.

(51) Int. Cl.
*C07C 45/50* (2006.01)
(52) U.S. Cl. .................................................. 568/454
(58) Field of Classification Search .................. 568/454
See application file for complete search history.

(56) References Cited

U.S. PATENT DOCUMENTS

| | | | |
|---|---|---|---|
| 4,483,802 A | | 11/1984 | Gartner et al. |
| 4,633,021 A | * | 12/1986 | Hanes .......................... 568/454 |
| 4,731,486 A | * | 3/1988 | Abatjoglou et al. .......... 568/454 |
| 4,935,550 A | * | 6/1990 | Miller et al. ................. 568/454 |
| 5,138,101 A | | 8/1992 | Devon |
| 5,180,854 A | * | 1/1993 | Abatjoglou et al. .......... 568/454 |
| 5,260,490 A | | 11/1993 | Forster et al. |
| 5,294,415 A | | 3/1994 | Lappe et al. |
| 5,648,554 A | | 7/1997 | Mori et al. |
| 5,696,297 A | | 12/1997 | Kneuper et al. |
| 5,756,854 A | | 5/1998 | Bahrmann et al. |
| 5,919,987 A | | 7/1999 | Kneuper et al. |
| 5,932,772 A | | 8/1999 | Argyropoulos et al. |
| 6,469,169 B1 | | 10/2002 | Seayad et al. |
| 6,685,896 B2 | | 2/2004 | Bohnen et al. |
| 7,196,230 B2 | | 3/2007 | Peng et al. |
| 7,294,729 B2 | | 11/2007 | Peng et al. |
| 7,351,868 B2 | | 4/2008 | Briggs et al. |
| 7,446,231 B2 | | 11/2008 | Peterson et al. |
| 7,485,759 B2 | | 2/2009 | Briggs et al. |
| 2005/0065379 A1 | | 3/2005 | Krumrey et al. |
| 2006/0193802 A1 | | 8/2006 | Lysenko et al. |

FOREIGN PATENT DOCUMENTS

| | | |
|---|---|---|
| BR | 9503081 A | 8/1996 |
| DE | 19908978 A1 | 9/2000 |
| EP | 0350921 A1 | 1/1990 |
| EP | 0695734 A1 | 2/1996 |
| EP | 0750602 A1 | 1/1997 |
| WO | WO-01/012581 A1 | 2/2001 |
| WO | WO-2004/096882 A1 | 11/2004 |
| WO | WO2004096744 * | 11/2004 |
| WO | WO-2006/020287 A1 | 2/2006 |
| WO | WO-2008/05740 A1 | 1/2008 |
| WO | WO-2008/024468 A2 | 2/2008 |
| WO | WO-2008/056993 A2 | 5/2008 |
| WO | WO-2008/073729 A2 | 6/2008 |

OTHER PUBLICATIONS

L. R. Snyder and J. J. Kirkland, *Introduction to Modern Liquid Chromatography*, Wiley-Interscience (John Wiley & Sons), 1974, pp. 215-218.
D. O'Conner and F. H. Verhoeck, *Journal of the American Chemical Society*, 80(2), (1958), pp. 288-290.
G. M. Kosolapoff and L. Maier, *Organic Phosphorous Compounds*, vol. 1, Wiley-Interscience (John Wiley & Sons), 1972, pp. 41-42.
J. H. Hilderbrand and R. L. Scott, *The Solubility of Non-Electrolytes*, Dover Publishers, NY, 1964, pp. 424-434.

* cited by examiner

*Primary Examiner*—Sikarl A Witherspoon

(57) ABSTRACT

A non-aqueous hydroformylation process with liquid catalyst recycle involving a hydroformylation step and one or more stages of phase separation to recover a high molecular weight aldehyde product with efficient recovery of rhodium catalyst. The process includes a hydroformylation step to prepare a non-aqueous hydroformylation reaction product composition comprising one or more aldehyde products, one or more conjugated polyolefins, a rhodium-organophosphorus ligand complex, free organophosphorus ligand, and an organic solubilizing agent for said complex and said free ligand, and thereafter one or more stages of phase separation using added water under a carbon monoxide gas, hydrogen gas, or a mixture thereof. The process requires a specific range of total pressure for the hydroformylation, a specific range of total pressure for at least one of the separation stages, and a minimum sum of the total pressure of the hydroformylation step and the total pressure of the separation stage containing said gas.

23 Claims, 1 Drawing Sheet

US 7,663,002 B2

HYDROFORMYLATION PROCESS AND PRODUCT SEPARATION WITH IMPROVED RECOVERY OF RHODIUM

CROSS-REFERENCE TO PRIOR APPLICATIONS

This application is a 371 filing of International Patent Application PCT/US2007/009452, filed Apr. 17, 2007, which claims the benefit of U.S. Provisional Patent Application No. 60/800,555, filed May 15, 2006.

BACKGROUND OF THE INVENTION

This invention pertains to a hydroformylation process to prepare a non-aqueous hydroformylation product composition containing one or more aldehyde products and a rhodium-organophosphorus ligand complex, and thereafter a phase separation of the one or more aldehyde products from the non-aqueous hydroformylation reaction product composition with improved separation and recovery of rhodium. The invention is suitably applied to non-aqueous reaction product compositions derived from hydroformylation of olefinically-unsaturated fatty acid esters (FAEs) obtained from seed oils.

Seed oils comprise a mixture of saturated and unsaturated fatty acid esters. The unsaturated fatty acid esters may contain from 1 to 3 olefinic bonds. As is well known, an ester comprises a product of a reaction between a carboxylic acid and an alcohol; therefore, an ester contains a molecular fragment derived from the carboxylic acid and a molecular fragment derived from the alcohol. In seed oils the alkanol is the trihydric alcohol glycerol; however, fatty acid esters of glycerol are difficult to process industrially due to their high molecular weight. Consequently, seed oils are typically transesterified with lower alkanols, which hereinafter refers to an alkanol of from one to about eight carbon atoms ($C_{1-8}$), such as methanol or ethanol, to obtain the corresponding mixture of saturated and unsaturated fatty acid esters of the lower alkanol, which due to their lower molecular weight are more amenable to chemical processing. As is known in the chemical art, "transesterification" refers to replacement of the alcohol fragment of an ester with a different alcohol fragment. Henceforth, unless otherwise noted, the words "unsaturated fatty acid ester(s)" will refer to unsaturated fatty acid ester(s) of a lower alkanol (transesterified seed oils), not the glycerol esters or the seed oils themselves.

The art describes the hydroformylation of a reactant olefin consisting of a mono-unsaturated fatty acid ester with carbon monoxide and hydrogen (e.g., synthesis gas) in the presence of a rhodium-organophosphorus ligand complex catalyst and free organophosphorus ligand to produce an aldehyde product having one additional carbon atom in the fatty acid chain ("monoformyl product") as compared with the reactant olefin. When the reactant olefin is a di-unsaturated or tri-unsaturated fatty acid ester, hydroformylation may occur at each olefinic unsaturation to yield dialdehydes ("diformyl product") and trialdehydes ("triformyl product"). The hydroformylation of a mixture of unsaturated fatty acid esters derived from seed oils produces a mixture of monoformyl, diformyl, and triformyl (aldehyde) products. Generally, not every olefinically-unsaturated bond is converted to aldehyde; thus the product derived from the aforementioned mixtures typically contains, in addition to one or more aldehyde products, a quantity of unconverted mono-unsaturated and poly-unsaturated (di- and/or tri-unsaturated) fatty acid esters. As an unavoidable side reaction, a portion of the unconverted poly-unsaturated fatty acid esters, which initially exist typically in unconjugated form, is isomerized to the corresponding conjugated isomers. One skilled in the art recognizes that an unconjugated olefin is one in which two C=C double bonds are separated by more than one C—C single bond; whereas a conjugated olefin is one in which two C=C double bonds are separated by only one C—C single bond.

The aforementioned mixtures of monoformyl, diformyl, and triformyl products derived from the hydroformylation of mixtures of unsaturated fatty acid esters can be reacted via hydrogenation or hydroamination processes to yield the corresponding alcohol, amine, or aminoalcohol derivatives, which can be condensed to form oligomeric polyols, polyamines, or polyaminoalcohols. The latter poly-functional compounds find utility in the manufacture of industrially useful polymers, most notably, polyurethanes. With regard to the aforementioned hydroformylation chemistry and subsequent derivatives, reference is made to International Patent Application Publications WO 2004-A1-096744 and WO 2004-A1-096882.

As illustrated by the above chemistry, seed oils can provide sustainable, alternative feedstocks to more conventional petroleum-based feedstocks for use in manufacturing industrially useful chemicals. Nevertheless, commercialization of chemical processes starting from the hydroformylation of fatty acid esters derived from seed oils will depend upon an efficient method of separating the resulting aldehyde product(s) from the hydroformylation reaction product composition. Moreover, commercialization also depends upon an efficient separation and recovery of rhodium. Even a small loss of rhodium into the aldehyde product would necessitate supplying make-up rhodium to the hydroformylation process; else the rhodium catalyst would be continuously depleted. Since rhodium is one of the most expensive metals, loss of rhodium is not acceptable. Furthermore, rhodium residue in the aldehyde product can lead to downstream problems; for example, rhodium is known to interfere with hydrogenation of the aldehyde product.

One skilled in the art may recognize that the hydroformylation of fatty acid esters is more readily conducted in a non-aqueous reaction medium, because fatty acid esters possess little, if any, solubility in water. Hydroformylations wherein the olefinically-unsaturated reactant and a rhodium-organophosphorus ligand complex catalyst are solubilized in a non-aqueous medium (i.e., organic solvent) are well known. Early references to non-aqueous processes disclosed rhodium-organophosphorus ligand complex catalysts wherein the organophosphorus ligand consisted of a neutral organophosphine or organophosphite, that is, an organophosphine or organophosphite free of an ionic charge, such as, triphenylphosphine. While such processes have been effective in hydroformylating lower olefins, namely olefins having from two to about 5 carbon atoms ($C_{2-5}$), their application is curtailed when hydroformylating high molecular weight olefins due to difficulties in separating high molecular weight aldehyde products from the hydroformylation reaction product composition. Distillation cannot be used for the separation, for at least one reason that the rhodium-organophosphorus ligand complex tends to degrade at the high temperatures needed for the distillation. Moreover, the problem is exacerbated when the product to be separated from the hydroformylation reaction product composition comprises aldehyde products derived from fatty acid esters, because the resulting aldehydes possess molecular weights entirely too large for separation by distillation methods.

With reference to the above and for the purposes of this invention, the terms "high molecular weight olefin" and "high molecular weight olefinically-unsaturated fatty acid ester"

are defined as an olefinic compound, or fatty acid ester as the case may be, having 7 or more carbon atoms. Likewise, the term "high molecular weight aldehyde product" is defined as an aldehyde product having 8 or more carbon atoms.

U.S. Pat. No. 5,180,854 discloses a process for phase separating and recovering a high molecular weight aldehyde product from a non-aqueous hydroformylation reaction product composition comprising the aldehyde product and a rhodium-organophosphorus ligand complex, free organophosphorus ligand, and an organic solubilizing agent for the complex and the free ligand. In the disclosed process, the organophosphorus ligand consists of an ionically-charged organophosphine, the term "ionically-charged" being described in detail hereinafter. The disclosed method involves adding water, and optionally a nonpolar solvent, to the non-aqueous hydroformylation reaction product composition and by phase separation obtaining a nonpolar phase consisting essentially of the aldehyde product and optional nonpolar solvent and a polar phase consisting essentially of the added water, the rhodium-organophosphorus ligand complex, the free organophosphorus ligand, and the organic solubilizing agent. The ionically-charged organophosphine ligand possesses an advantageous solubility in water; thus rhodium and ligand are separated from the high molecular weight aldehyde product. Being insoluble in water, the aldehyde product remains in the nonpolar phase.

While the method of U.S. Pat. No. 5,180,854 has been adopted for use with reaction product compositions derived from hydroformylating high molecular weight mono-olefins, we have now found that the method remains inadequate when applied to reaction product compositions derived from the hydroformylation of mixtures of high molecular weight mono-olefins and polyolefins, as are found in mixtures of unsaturated fatty acid esters derived from seed oils. We have further recognized that when the reaction product composition contains one or more aldehyde products and one or more conjugated polyolefins, then after phase separation, the quantity of rhodium metal in the nonpolar phase containing the aldehyde products is unacceptably high. The words "unacceptably high" mean that the concentration of rhodium in the nonpolar phase is greater than about 3.0 parts per million (ppm) by weight, based on the weight of the nonpolar phase.

We have further found that rhodium can be recovered with an acceptable efficiency from a hydroformylation reaction product composition containing high molecular weight conjugated polyolefins, if the reaction product composition is produced in a hydroformylation process operating at synthesis gas pressures of 600 psia (4,137 kPa) or higher. Operating the hydroformylation at a high pressure is not desirable, however, because higher pressure is associated with higher operating costs, more expensive equipment, and waste of resources.

In view of the above, it would be desirable to discover a non-aqueous hydroformylation process, preferably in continuous operation, combined with an improved separation stage for separating one or more aldehyde products from a non-aqueous hydroformylation reaction product composition comprising the one or more aldehyde products and a rhodium-organophosphorus ligand complex. It would be more desirable if the hydroformylation process employed low operating pressures, for example, pressures ranging from about 250 psia (1,724 kPa) to about 450 psia (3,103 kPa), so as to avoid the costs of higher pressurized processes. It would be even more desirable if the separation stage were to separate and recover rhodium from the hydroformylation reaction product composition with a high degree of efficiency. For the purposes of this invention, the words "high degree of efficiency" mean that after implementing the separation an aldehyde-containing nonpolar phase is recovered containing less than about 1.0 ppm rhodium, by weight, based on the weight of the nonpolar phase. Finally, it would be most desirable if the method could provide a high efficiency of rhodium separation and recovery when using mixtures of high molecular weight aldehydes containing conjugated polyolefins as found, for example, in reaction product compositions derived from the hydroformylation of unsaturated fatty acid esters obtained from seed oils.

If the aforementioned effects could be achieved, rhodium would be concentrated essentially in an aqueous phase from which the rhodium could be recovered for direct catalyst recycle to the hydroformylation process. Such a separation method would also provide for a purer aldehyde product, would minimize the disadvantageous effects of residual rhodium on downstream aldehyde processing, and would minimize the amount of make-up rhodium supplied to the hydroformylation process. Moreover, a low pressure hydroformylation process would minimize engineering costs and waste of resources. As a consequence, commercialization of industrially useful processes starting from the hydroformylation of unsaturated fatty acid esters derived from seed oils may move closer to realization.

SUMMARY OF THE INVENTION

The invention disclosed herein provides for a non-aqueous hydroformylation process for producing high-molecular weight aldehydes with an improved separation stage and high efficiency recovery of rhodium. The subject invention comprises:

(a) hydroformylating a mixture of olefinically-mono-unsaturated and olefinically-poly-unsaturated compounds with carbon monoxide and hydrogen in the presence of a rhodium-organophosphorus ligand complex, a free organophosphorus ligand, and a polar organic solubilizing agent for said complex and said free ligand, in a hydroformylation reactor at a total pressure ranging from about 250 psia (1,724 kPa) to about 450 psia (3,103 kPa); and obtaining therefrom a non-aqueous hydroformylation reaction product composition comprising one or more aldehyde products, one or more conjugated polyolefins, a rhodium-organophosphorus ligand complex, free organophosphorus ligand, and a polar organic solubilizing agent for said complex and said free ligand; wherein one or more aldehyde products comprise greater than about 8 carbon atoms; wherein one or more olefinically-mono-unsaturated olefins, one or more olefinically-poly-unsaturated olefins, and one or more conjugated polyolefins comprise greater than about 7 carbon atoms; and the organophosphorus ligand comprises an ionically-charged organophosphine ligand; and (b) separating said hydroformylation reaction product composition by contacting said composition with water and optionally a nonpolar solvent under conditions sufficient to obtain by one or more stages of phase separation a nonpolar phase comprising the one or more aldehyde products, the one or more conjugated polyolefins, the optional nonpolar solvent, and rhodium in a concentration less than about 1.0 ppm by weight, based on weight of the nonpolar phase, and a polar phase comprising the rhodium-organophosphorus ligand complex, the free organophosphorus ligand, the polar organic solubilizing agent, and added water; the contacting with water and optional nonpolar solvent in at least one of the stages of phase separation occurring in the presence of a carbon monoxide-containing gas, a hydrogen-containing gas, or a mixture thereof at a total pressure greater than about 20 psia (138 kPa) and less than about 400 psia (2,758 kPa), provided that the sum of total pressure in the hydroformylation step (a) and total pressure in the at least one separation stage (b) containing said gas is greater than about 360 psia (2,482 kPa).

In another aspect, this invention further comprises (c) removing the added water from the polar phase, and recycling said resulting polar non-aqueous phase consisting essentially of the rhodium-organophosphorus ligand complex, the free organophosphorus ligand, and the polar organic solubilizing agent back to hydroformylation step (a).

The process of this invention, as described hereinabove, is usefully applied to the separation of high molecular weight aldehyde products from a hydroformylation reaction product composition comprising the one or more aldehyde products and a rhodium-organophosphorus ligand complex. Preferably, the hydroformylation reaction product composition is derived from the hydroformylation of a mixture of high molecular weight mono-olefinically-unsaturated and poly-olefinically-unsaturated fatty acid esters, as preferably may be derived, for example, from seed oils. Surprisingly, this invention provides for recovery of rhodium with a high degree of efficiency from hydroformylation reaction product compositions where such product compositions further comprise conjugated polyolefins, as by-products typically found in the hydroformylation products obtained from unsaturated fatty acid esters derived from seed oils.

Advantageously, the process of this invention provides for aldehyde product(s) of improved purity resulting from improved separation of rhodium, such that the concentration of rhodium in the aldehyde-containing nonpolar phase is less than about 1.0 ppm by weight, based on the weight of the nonpolar phase. Such purer aldehyde product(s) minimize the adverse effects of residual rhodium in downstream processing of the aldehyde product(s). In the process of this invention, rhodium is essentially completely recovered into the aqueous polar phase; where rhodium can be concentrated into a rhodium-containing or catalyst-containing solution of the polar organic solubilizing agent for recycle back to the hydroformylation process. Thus, the process of this invention also provides for conservation of rhodium values by reducing rhodium losses to the aldehyde product and reducing make-up rhodium to the hydroformylation process. Finally, the separation stage of this invention is joined to a low pressure hydroformylation process operating at a pressure between about 250 psia (1,724 kPa) and about 450 psia (3,103 kPa) such that operating costs of the overall process are lower as compared with a hydroformylation operating at a higher pressure of greater than about 500 psia (3,447 kPa).

BRIEF DESCRIPTION OF THE DRAWING

The FIGURE is a schematic block flow diagram of an embodiment of the invention as it pertains to the separation and recovery of an aldehyde product from a continuous non aqueous hydroformylation reaction product composition with liquid catalyst recycle to the hydroformylation reactor.

DETAILED DESCRIPTION OF THE INVENTION

Figure 1:
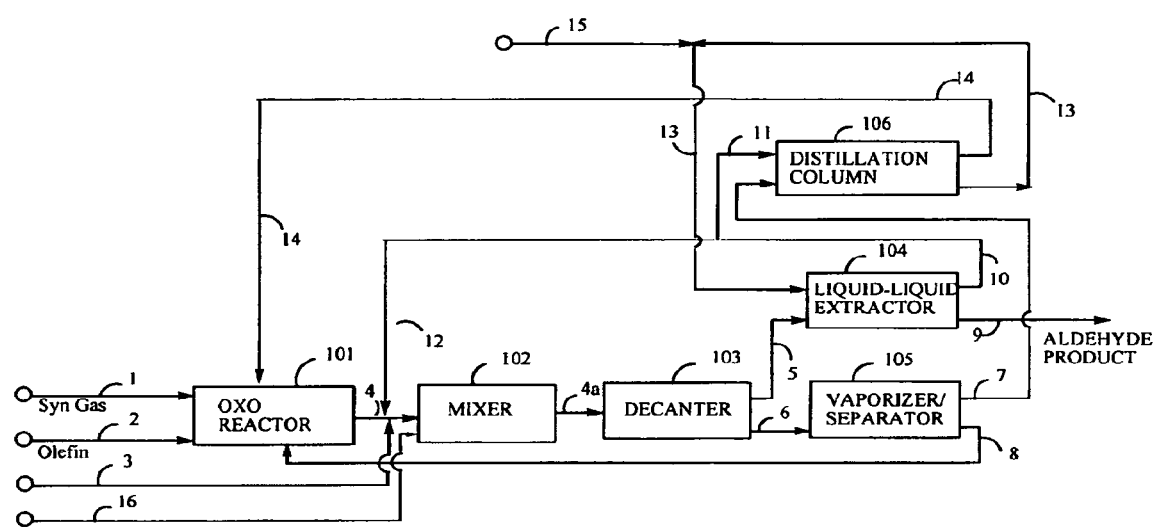

As summarized hereinabove, this invention is seen to provide for a non-aqueous hydroformylation process for producing aldehydes with an improved separation stage for recovery of the aldehyde product(s) and high efficiency recovery of rhodium. The subject invention comprises:

(a) hydroformylating a mixture of olefinically-mono-un-saturated and olefinically-poly-unsaturated compounds with carbon monoxide and hydrogen in the presence of a rhodium-organophosphorus ligand complex, a free organophosphorus ligand, and a polar organic solubilizing agent for said complex and said free ligand, in a hydroformylation reactor at a total pressure ranging from about 250 psia (1,724 kPa) to about 450 psia (3,103 kPa); and obtaining therefrom a non-aqueous hydroformylation reaction product composition comprising one or more aldehyde products, one or more conjugated polyolefins, a rhodium-organophosphorus ligand complex, free organophosphorus ligand, and a polar organic solubilizing agent for said complex and said free ligand; wherein one or more aldehyde products comprise greater than about 8 carbon atoms; wherein one or more olefinically-mono-unsaturated olefins, one or more olefinically-poly-unsaturated olefins, and one or more conjugated polyolefins comprise greater than about 7 carbon atoms; and the organophosphorus ligand comprises an ionically-charged organophosphine ligand; and (b) separating said hydroformylation reaction product composition by contacting said composition with water and optionally a nonpolar solvent under conditions sufficient to obtain by one or more stages of phase separation a nonpolar phase comprising the one or more aldehyde products, the one or more conjugated polyolefins, the optional nonpolar solvent, and rhodium in a concentration less than about 1.0 ppm by weight, based on the weight of the nonpolar phase, and a polar phase comprising the rhodium-organophosphorus ligand complex, the free organophosphorus ligand, the polar organic solubilizing agent, and added water; the contacting with water and optional nonpolar solvent in at least one stage of phase separation occurring in the presence of a carbon monoxide-containing gas, a hydrogen-containing gas, or a mixture thereof at a total pressure greater than about 20 psia (138 kPa) and less than about 400 psia (2,758 kPa); provided that the sum of the total pressure of the hydroformylation step (a) and the total pressure in the at least one separation step (b) containing said gas, is greater than about 360 psia (2,482 kPa).

In another aspect, the process of this invention further comprises step (c) removing the added water from the polar phase and recycling the resulting polar non-aqueous phase consisting essentially of the rhodium-organophosphorus ligand complex, the free organophosphorus ligand, and the polar organic solubilizing agent back to hydroformylation step (a).

In a preferred embodiment, the process of this invention is conducted in a continuous mode of operation.

In another preferred embodiment of this invention, the hydroformylation reaction product composition is derived from the non-aqueous hydroformylation of a mixture of olefinically-mono-unsaturated and olefinically poly-unsaturated fatty acid esters with carbon monoxide and hydrogen in the presence of a rhodium-ionically-charged organophosphine ligand complex catalyst, free ionically-charged organophosphine ligand, and a solubilizing agent for said complex catalyst and said free ligand. More preferably, said mixture of olefinically-unsaturated fatty acid esters is derived from the transesterification of a seed oil with a $C_{1-8}$ alkanol, most preferably, an alkanol having from one to about four carbons ($C_{1-5}$). Most preferably, the seed oil is soy, castor, canola, or sunflower oil, or a mixture thereof.

In yet another preferred embodiment of this invention, in step (b) the contacting of the hydroformylation reaction product composition with water and the optional nonpolar solvent is conducted at a temperature greater than about 50° C., and preferably, at a temperature greater than about 60° C. and less than about 130° C.

As discussed above, this invention is directed in part to separating one or more aldehyde products from a non-aqueous hydroformylation reaction product composition via phase separation. The term "non-aqueous hydroformylation reaction product composition," as employed herein, means any non-aqueous composition comprising one or more aldehydes, one or more conjugated polyolefins, a rhodium-organophosphorus ligand complex, free organophosphorus ligand, and a polar organic solubilizing agent for said complex and said free ligand; and wherein, preferably, the organophosphorus ligand of said complex and said free organophosphorus ligand is an ionically-charged organophosphine ligand.

For the purposes of this invention, the term "non-aqueous," as employed herein with regard to the hydroformylation reaction product composition, means that the hydroformylation reaction product composition fed to the separation stage is free or essentially free of water, which means that any water, if present at all, is not present in an amount sufficient to cause the hydroformylation reaction product composition to be considered as encompassing a separate aqueous or water phase or layer in addition to an organic phase. Of course, in the separation stage water is deliberately added to the hydroformylation reaction product composition, after which addition the composition is no longer considered to be non-aqueous.

The term "aldehyde," as used herein, is given its well-known meaning in the field of organic chemistry. Specifically, since the hydroformylation employs carbon monoxide and hydrogen, reference to the product "aldehyde" is synonymous with the presence of a "formyl" substituent (—CH=O).

The term "conjugated polyolefin," as used herein, refers to an organic compound comprising two or more olefinic bonds (i.e., two or more carbon=carbon double bonds), at least two of which are in conjugated arrangement. As mentioned earlier, the term "conjugated" refers to two C=C double bonds that are separated by one C—C single bond. In contrast, an "unconjugated" arrangement refers to two C=C double bonds that are separated by two or more C—C single bonds. The one or more conjugated polyolefins may be derived from any conjugated or unconjugated polyolefin, such as, a di-unsaturated or tri-unsaturated olefin, present in the olefinic feed to the hydroformylation process from whence the hydroformylation reaction product composition may be derived. Under hydroformylation process conditions, a fraction of the unconjugated polyolefins in the olefinic feed to the hydroformylation process may be and typically is isomerized to the corresponding conjugated isomers The term "ligand" refers to any neutral molecule or charged ion that is bound to or complexed with a metal of a metal-ligand complex. In this invention, the metal is rhodium. With reference to the ligand, the term "ionically-charged" means that the ligand contains at least one negatively-charged anionic substituent; each such substituent being counter-balanced by a positively-charged cation. As a preferred example, the ionically-charged substituent may be a monovalent anionic sulfonyl group attached to any element of the ligand and counter-balanced by a monovalent cation, such as sodium ion.

The term "free organophosphorus ligand," as used herein, means that the organophosphorus ligand is not complexed with, tied to, or bound to a rhodium atom.

Of course, it should be understood that the non-aqueous hydroformylation reaction product composition employable herein can and normally will contain additional components such as those that have either been deliberately employed in the non-aqueous hydroformylation process or those formed in situ during the hydroformylation process. Examples of such additional components include carbon monoxide and hydrogen gases, and in-situ formed products, such as, saturated hydrocarbons and high boiling liquid aldehyde condensation by-products, as well as other inert co-solvent materials or hydrocarbon additives, as may be employed.

The high molecular weight aldehyde products which are contained in the non-aqueous hydroformylation reaction product composition and which can be removed therefrom by the phase separation process of this invention comprise aldehydes containing from about 8 to about 40 carbon atoms. Such aldehydes typically encompass the corresponding aldehyde products obtained upon hydroformylating olefinic compounds containing from about 7 to about 39 carbon atoms. The olefinic compounds may be of straight-chain or branched-chain structure and may contain one or more ethylenically unsaturated groups, as noted hereinbefore. Preferably, the olefins are straight-chain internal olefins. Moreover such olefinic compounds, and consequently their corresponding aldehyde hydroformylation products, may contain one or more substituents that do not substantially interfere adversely with the hydroformylation and the subsequent phase separation process of this invention. Further description to suitable substituents are presented hereinafter; but ester substituents are preferred. Alkyl alkenoates (unsaturated alkyl esters) having 7 or more carbon atoms are even more preferred olefinic compounds for use in the hydroformylation process from whence the hydroformylation reaction product composition may be derived.

The most preferred olefinically-unsaturated compounds used to prepare the hydroformylation reaction product composition comprise a mixture of unsaturated fatty acid esters derived from the transesterification of seed oils with a $C_{1-8}$ alkanol. Such mixtures contain olefinically mono-unsaturated, di-unsaturated, and tri-unsaturated fatty acid esters. Feedstocks derived from seed oils also contain varying amounts of saturated fatty acid esters, which are non-reactive in hydroformylation processes. The seed oil may be selected from any natural or genetically modified (GMO) plant or vegetable seed oil, non-limiting examples of which include castor, soybean, olive, peanut, rapeseed, corn, sesame, cottonseed, canola, safflower, linseed, sunflower, and high oleic oils, as well as genetically-modified variations of the aforementioned oils, and mixtures thereof. Preferably, the seed oil is selected from soybean (natural and GMO), castor, sunflower (including high oleic), and canola (including high oleic) oils.

Typically, the olefinically-unsaturated feedstock comprises one or more fatty acid esters each consisting of a fatty acid chain of at least about 6, preferably, greater than about 10, and more preferably, greater than about 12 carbon atoms. Typically, the fatty acid chain contains less than about 40, preferably, less than about 35, and more preferably, less than about 30 carbon atoms. The fatty acid chain may be straight or branched and substituted with one or more substituents, provided that the substituents do not materially interfere with the hydroformylation and phase separation processes described herein. Non-limiting examples of suitable substituents include alkyl moieties, preferably $C_{1-10}$ alkyl moieties, for example methyl, ethyl, propyl, and butyl; cycloalkyl moieties, preferably, $C_{4-8}$ cycloalkyl; phenyl; benzyl; $C_{7-16}$ alkaryl and aralkyl moieties; hydroxy, ether, ester, keto, and halide (preferably, chloro and bromo) substituents.

The feedstock mixture of fatty acid esters employed in the hydroformylation process to prepare the hydroformylation reaction product composition preferably comprises greater than about 65 percent, preferably, greater than about 70 percent, and more preferably, greater than about 80 percent unsaturated fatty acid esters by weight. More preferably, the feedstock mixture of fatty acid esters comprises from greater than about 10 to less than about 95 percent mono-unsaturated fatty acid esters by weight; from greater than about 4 to less than about 60 percent di-unsaturated fatty acid esters by weight; and from greater than about 1 to less than about 70 percent tri-unsaturated fatty acid esters, by weight.

Non-limiting examples of suitable olefinically-unsaturated fatty acid segments that may be found in the olefinically-unsaturated ester feedstock include 3-hexenoic (hydrosorbic), trans-2-heptenoic, 2-octenoic, 2-nonenoic, cis- and trans-4-decenoic, 9-decenoic (caproleic), 10-undecenoic (undecylenic), trans-3-dodecenoic (linderic), tridecenoic, cis-9-tetradeceonic (myristoleic), pentadecenoic, cis-9-hexadecenoic (cis-9-palmitoelic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-1-octadecenoic, trans-11-octadecenoic (vaccenic), cis-5-eicosenoic, cis-9-eicosenoic (godoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), cis-5-docosenoic, cis-5,13-docosadienoic, 12,13-epoxy-cis-9-octadecenoic (vernolic), and 14-hydroxy-cis-11-eicosenoic acid (lesquerolic) acids. A preferred unsaturated fatty acid segment contains no conjugated double bonds. A most preferred unsaturated fatty acid segment is oleic acid.

As mentioned hereinbefore, the feedstock mixture of olefinically-unsaturated fatty acid esters, which may be hydroformylated to prepare the hydroformylation reaction product composition, is obtained by transesterifying a seed oil with a lower alkanol. The carbon atoms in the alcohol may be arranged in a straight-chain or a branched structure and may be substituted with a variety of substituents, such as those previously disclosed hereinabove in connection with the fatty acid segment, provided that such substituents do not materially interfere with the hydroformylation subsequent phase separation process of this invention. Preferably, the lower alkanol is a $C_{1-8}$ alkanol, more preferably, a $C_{1-4}$ alkanol. Even more preferably, the lower alkanol is selected from methanol, ethanol, and isopropanol, most preferably, methanol. The art adequately discloses methods of transesterifying seed oils, as found, for example, in WO 2001/012581, DE 19908978, and BR 953081. We note that the art may refer to transesterification with methanol as "methanolysis" and transesterification with ethanol as "ethanolysis."

Non-aqueous hydroformylation process conditions capable of converting the one or more olefinically-unsaturated compounds, preferably, the mixture of olefinically-unsaturated fatty acid esters, to the non-aqueous hydroformylation reaction product composition are not narrowly critical and may be found in the prior art. For instance, generally, it is preferred to employ non-aqueous hydroformylation reaction product compositions derived from corresponding non-aqueous hydroformylation reaction processes that employ the operational features taught in U.S. Pat. No. 4,731,486, U.S. Pat. No. 4,633,021, U.S. Pat. No. 4,731,486, WO 2004/096744, the disclosures of which are incorporated herein by reference. In accordance with the aforementioned references, the reaction conditions for effecting such non-aqueous hydroformylation processes may be those heretofore conventionally used and may comprise a reaction temperature greater than about 40° C., preferably, greater than about 50° C., and more preferably, greater than about 60° C. The reaction temperature is typically less than about 200° C., preferably, less than about 150° C., and more preferably, less than about 130° C. For such hydroformylation processes, generally, the total reactor pressure may range from about 100 psia (689 kPa) to about 5,000 psia (34.5 MPa). For the purposes of this invention, preferably, the total reactor pressure is greater than about 250 psia (1,724 kPa), and more preferably, greater than about 275 psia (1,896 kPa). Preferably, the total reactor pressure is less than about 600 psia (4,137 kPa), and more preferably, less than about 450 psia (3103 kPa). Carbon monoxide partial pressure of the non-aqueous hydroformylation process is typically greater than about 50 psia (345 kPa), and preferably, greater than about 125 psia (862 kPa). The carbon monoxide partial pressure of the non-aqueous hydroformylation process is typically less than about 500 psia (3,448 kPa), and preferably, less than about 300 psia (2,069 kPa). Hydrogen partial pressure of the non-aqueous hydroformylation process is typically greater than about 50 psia (345 kPa), and preferably, greater than about 100 psia (689 kpa). The hydrogen partial pressure of the non-aqueous hydroformylation process is typically less than about 500 psia (3,448 kPa), and preferably, less than about 300 psia (2,069 kPa). In general a $H_2$:CO molar ratio of gaseous hydrogen to carbon monoxide may range from about 1:5 to 5:1 or higher, the more preferred hydrogen to carbon monoxide molar ratio being about 1:1.

The hydroformylation process is preferably conducted in the presence of rhodium in an amount ranging from about 10 ppm to about 1,000 ppm, preferably, from about 10 ppm to about 800 ppm, by weight, calculated as metallic rhodium and based on the weight of the liquid non-aqueous hydroformylation reaction medium. The organophosphorus ligand is present in an amount typically greater than about 0.2 percent, and preferably, greater than about 0.5 percent, by weight, based on the weight of the liquid non-aqueous hydroformylation reaction medium. The organophosphorus ligand is present in an amount typically less than about 4.0 percent, and preferably, less than about 2.0 percent, by weight, based on the weight of the liquid non-aqueous hydroformylation reaction medium. The organic solubilizing agent comprises typically from about 15 percent to about 50 percent, and more preferably, from about 10 percent to about 30 percent, by weight, based on the weight of the liquid non-aqueous hydroformylation reaction medium. Moreover, while it is clear that the non-aqueous hydroformylation process can be conducted in a batch type process, a continuous process with a liquid catalyst recycle to the hydroformylation reactor is more desirable.

The total amount of the one or more aldehyde products present in the non-aqueous hydroformylation reaction product composition, employable as the feed to the one or more phase separation stages, may range from about 10 to about 90 weight percent, based on the weight of the hydroformylation reaction product composition. Preferably, the total amount of the one or more aldehyde products present in the non-aqueous hydroformylation reaction product composition, employable as the feed to the one or more phase separation stages, may range from about 20 to about 80 weight percent, based on the weight of the hydroformylation reaction product composition.

The total amount of the one or more conjugated polyolefins present in the non-aqueous hydroformylation reaction product composition, employable as the feed to the one or more phase separation stages, may range from about 0.1 to about 20 weight percent, based on the weight of the hydroformylation reaction product composition. Preferably, the total amount of the one or more conjugated polyolefins in the non-aqueous hydroformylation reaction product composition, employable as the feed to the one or more phase separation stages, ranges from about 0.5 to about 5 weight percent, based on the weight of the hydroformylation reaction product composition.

As a further component, the hydroformylation reaction product composition comprises an organophosphorus ligand which exists either bound to rhodium in a complex or unbound to rhodium (free). Specifically, the organophosphorus ligand comprises an ionically-charged organophosphine ligand. Preferably, the organophosphine ligand consists essentially of a monosulfonated tertiary phosphine metal salt having the general formula:

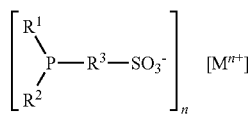

wherein $R^1$ and $R^2$ each individually represent a radical containing from 1 to about 30 carbon atoms selected from the group consisting of alkyl, aryl, alkaryl, aralkyl and alicyclic radicals; wherein $R^3$ represents a divalent alkylene radical having from 2 to about 12, preferably 2 to about 5 carbon atoms, or a divalent 1,3-phenylene radical; wherein M represents a metal cation selected from the group consisting of alkali and alkaline earth metals; and wherein n has a value of 1 or 2 corresponding to the valance of the particular metal cation represented by M. As seen in the formula hereinabove, the sulfonate group is a negatively charged anion (−1), which for charge balance requires a positively charged cation. Hence, the skilled artisan will understand the term "ionically-charged" to mean that the organophosphorus ligand contains a positively and negatively charged ion pair.

Illustrative radicals represented by the $R^1$ and $R^2$ in the above monosulfonated tertiary phosphine metal salt formula include monovalent hydrocarbon radicals containing from 1 to 30 carbon atoms, e.g., alkyl radicals including linear or branched, primary, secondary or tertiary alkyl radicals, such as methyl, ethyl, n-propyl, isopropyl, butyl, sec-butyl, t-butyl, t-butylethyl, t-butylpropyl, n-hexyl, amyl, sec-amyl, t-amyl, 2-ethylhexyl, n-octyl, iso-octyl, decyl, dodecyl, octadecyl, and eicosyl; aryl radicals, such as phenyl and naphthyl; aralkyl radicals, such as benzyl and phenylethyl; alkaryl radicals, such as tolyl and xylyl; and alicyclic radicals, such as cyclopentyl, cyclohexyl, cyclooctyl, and cyclohexylethyl. The aforementioned examples are not meant to be limiting in any way. Moreover, such monovalent hydrocarbon radicals may be substituted with any substituent that does not unduly adversely affect the desired results of this invention. Illustrative substituents that may be on the hydrocarbon radicals include for example silyl radicals such as —Si(R$^9$)$_3$, amino radicals such as —N(R$^9$)$_2$, acyl radicals such as —C(O)R$^9$, acyloxy radicals such as —OC(O)R$^9$, amido radicals such as —CON(R$^9$)$_2$ and —N(R$^9$)COR$^9$, sulfonyl radicals such as —SO$_2$R$^9$, alkoxy radicals such as —OR$^9$, thionyl radicals such as —SR$^9$, phosphonyl radicals such as —P(O)(R$^9$)$_2$, as well as, halogen, nitro, cyano, trifluoromethyl, and hydroxy radicals, wherein each R$^9$ individually represents the same or different substituted or unsubstituted monovalent hydrocarbon radical having the same meaning as defined for $R^1$ and $R^2$ above, provided that in amino substituents such as —N(R$^9$)$_2$, each R$^9$ taken together can also represent a divalent bridging group that forms a heterocyclic radical with the nitrogen atom, and in amido substituents such as —C(O)N(R$^9$)$_2$ and —N(R$^9$)COR$^9$ each R$^9$ bonded to N can also be hydrogen. Of course, it should be understood that the $R^1$ and $R^2$ groups in a particular given metal salt ligand may be the same or different.

When $R^3$ in the above formula represents a divalent 1,3-phenylene radical, preferably the monovalent hydrocarbon radicals represented by $R^1$ and $R^2$ are selected from the group consisting of alkyl radicals having from $C_1$ to $C_{20}$ carbon atoms, aryl radicals having from $C_6$ to $C_{12}$ carbon atoms, and alicyclic radicals having from $C_5$ to $C_{12}$ carbon atoms. More preferably, the $R^1$ and $R^2$ groups are each individually a branched chain alkyl radical having from about 3 to about 9 carbon atoms (such as isopropyl, t-butyl, etc.), or a phenyl or a cyclohexyl radical. Most preferably, the $R^1$ and $R^2$ radicals in a given monosulfonated tertiary phosphine metal salt each individually represent a phenyl or cyclohexyl radical, especially cyclohexyl, when $R^3$ is a divalent 1,3-phenylene radical.

When $R^3$ in the above formula represents a divalent alkylene radical, preferably $R^1$ represents an aryl radical having from $C_6$ to $C_{12}$ carbon atoms or an alicyclic radical having from $C_5$ to $C_{12}$ carbon atoms and $R^2$ represents an alkyl radical having from $C_1$ to $C_{20}$ carbon atoms, an aryl radical having from $C_6$ to $C_{12}$ carbon atoms or an alicyclic radical having from $C_5$ to $C_{12}$ carbon atoms. More preferably $R^1$ is a phenyl or cyclohexyl radical and $R^2$ is a branched chain alkyl radical having from about 3 to about 9 carbon atoms (such as isopropyl, t-butyl, etc.), a phenyl or a cyclohexyl radical. Most preferably the $R^1$ and $R^2$ radicals in a given monosulfonated tertiary phosphine metal salt each individually represent a phenyl or a cyclohexyl radical, especially cyclohexyl when $R^3$ is a divalent alkylene radical having from about 2 to about 5 carbon atoms, especially 1,3-propylene or 1,4-butylene.

As noted, M in the monosulfonated tertiary phosphine metal salt ligand formula hereinabove represents a metal cation selected from the group consisting of alkali and alkaline earth metals. Illustrative alkali metals include lithium (Li+), sodium (Na+), potassium (K+), cesium (Cs+) and rubidium (Rb+), while illustrative alkaline earth metals include calcium (Ca++), barium (Ba++), magnesium (Mg++) and strontium (Sr++). Moreover as noted above by the definition of n, the metal salt ligand may contain one or two monosulfonated tertiary phosphine anionic molecules corresponding to the positive valence of the metal cation M.

The more preferred class of monosulfonated tertiary phosphine metal salt ligands employable herein is that wherein $R^3$ represents a divalent 1,3-phenylene radical, which has the general formula:

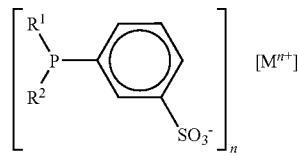

wherein $R^1$, $R^2$, M and n may be the same as defined above, in contrast to those of the class wherein $R^3$ represents a divalent alkylene radical, which has the general formula:

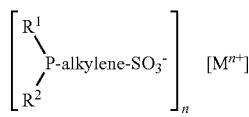

wherein the divalent alkylene radical contains from 2 to 12 carbon atoms, and $R^1$, $R^2$, M and n are the same as defined above.

Illustrative preferred monosulfonated tertiary phosphine metal salt ligands include all of such compounds listed in U.S. Pat. No. 5,180,854, incorporated herein by reference. A most preferred ionic tertiary organophosphine ligand is dicyclohexylphenylphosphine monosulfonate metal salt. Such types of monosulfonated tertiary phosphine metal salt ligands employable in this invention and/or methods for their manufacture are well known, as seen, for example, in the procedures described in *Journal of the Chemical Society*, pp. 276-288 (1958), U.S. Pat. No. 4,483,802, U.S. Pat. No. 4,731,486, U.S. Pat. No. 5,180,854, and WO 2004/096744, incorporated herein by reference. Such ligands wherein $R^3$ in Formula (I) above is a divalent alkylene radical may be prepared, for example, by conventional nucleophilic substitution reactions such as taught in *Organic Phosphorus Compounds*, Vol. 1, by G. M. Kosolapoff and L. Maier, pp. 41-2 (1972), Wiley-Interscience.

Another component in the non-aqueous hydroformylation reaction product composition is a rhodium-organophosphorus ligand complex, which primarily corresponds to the rhodium-organophosphorus ligand complex catalyst employed in the non-aqueous hydroformylation reaction process from which the hydroformylation reaction product composition may be derived. However, it is to be noted that the successful practice of this invention does not depend and is not predicated upon the exact structure of the rhodium-organophosphorus complex species present in the non-aqueous hydroformylation reaction product composition. Such species may be present in their mononuclear, dinuclear and or higher nuclearity forms. Indeed the exact structure may not be known. Although it is not intended herein to be bound to any theory or mechanistic discourse, it is believed that the rhodium-organophosphorus ligand complex may in its simplest form consist essentially of rhodium in complex combination with carbon monoxide and the ionically-charged organophosphine ligand. The composition of the rhodium-organo-phosphorus ligand complex may also contain an additional inorganic or organic ligand, either neutral or anionic, and satisfying the coordination sites or nuclear charge of the rhodium metal. Hydrogen, for example, might also be bound to the rhodium.

Rhodium-organophosphorus ligand complex hydroformylation catalysts may be prepared by methods known in the art; for instance, preformed rhodium (hydrido) carbonyl monosulfonated tertiary phosphine metal salt ligand complexes may be prepared and introduced with a solubilizing agent, if necessary, into the reaction medium of the non-aqueous hydroformylation process. More commonly the rhodium-organophosphorus ligand complex is derived from a metal catalyst precursor, such as rhodium dicarbonyl acetylacetonate, $Rh_2(CO)_3$, $Rh_4(CO)_{12}$, $Rh_6(CO)_{16}$, $Rh(NO_3)_3$, which may be introduced along with the ionic tertiary organophosphine ligand, and an added organic solubilizing agent for the in-situ formation of the active catalyst for the hydroformylation process.

The amount of rhodium-organophosphorus ligand complex present in the non-aqueous hydroformylation reaction product composition fed to the separation stage generally corresponds to the amount of the corresponding complex present in the reaction medium of the non-aqueous hydroformylation process from which said reaction product composition is derived. Generally, the amount of rhodium-organophosphorus ligand complex present in the reaction medium of a given hydroformylation process is expressed in terms of the amount of rhodium present calculated as rhodium metal. Rhodium concentrations in the range from about 10 ppm to about 1000 ppm, and preferably from about 10 ppm to about 800 ppm, of rhodium calculated as rhodium metal should be sufficient for the hydroformylation process. Accordingly, the amount of rhodium-organophosphorus ligand complex present in a given non-aqueous hydroformylation reaction product composition may be expressed in the same way and may correspondingly range from about 10 ppm to about 1000 ppm, preferably from about 10 ppm to about 800 ppm, of rhodium calculated as rhodium metal.

The amount of organophosphorus ligand present in the non-aqueous hydroformylation reaction product composition is typically similar to that amount of ligand present in the hydroformylation reaction medium from which the non-aqueous hydroformylation reaction product composition is derived. Preferably, the amount of organophosphorus ligand in the non-aqueous hydroformylation reaction product composition is greater than about 0.2 percent, and more preferably, greater than about 0.5 percent, by weight, based on the weight of the non-aqueous hydroformylation reaction product composition. Preferably, the amount of organophosphorus ligand in the non-aqueous hydroformylation reaction product composition is less than about 4.0 percent, and more preferably, less than about 2.0 percent, by weight, based on the weight of the non-aqueous hydroformylation reaction product composition.

As noted above, the ionically-charged organophosphine ligands defined herein, preferably, the monosulfonated tertiary phosphine metal salt ligands, are employed in this invention as both the phosphorus ligand of the rhodium-organophosphorus ligand complex and as the free organophosphorus ligand present in the non-aqueous hydroformylation reaction product composition. While the ionically-charged organophosphine ligand of the rhodium-ligand complex and the free ligand are normally identical, they may be different; and alternatively, mixtures of two or more ionically-charged organophosphine ligands may be employed, if desired. The amount of free organophosphorus ligand present in the non-aqueous hydroformylation reaction product composition fed to the separation stage will generally correspond to the amount of corresponding free organophosphorus ligand present in the reaction medium of the non-aqueous hydroformylation process from which the hydroformylation product composition may be derived. For instance, since the hydroformylation process may be carried out in any excess amount of free organophosphorus ligand, such as, at least one mole of free monosulfonated tertiary phosphine metal salt ligand per mole of rhodium present in the reaction medium, the amount of free organophosphorus ligand present in the non-aqueous hydroformylation product composition can also be any corresponding excess amount. In general, amounts of free organophosphorus ligand of from about 2 to about 100, and preferably from about 5 to about 20 moles per mole of rhodium metal are suitable for both the hydroformylation process and the corresponding hydroformylation reaction product composition derived therefrom.

The non-aqueous hydroformylation reaction product composition employable in this invention also contains an organic solubilizing agent corresponding to that employed for solubilizing the rhodium-organophosphorus ligand complex and free organophosphorus ligand in the reaction medium of the non-aqueous hydroformylation process from which said product composition may be derived. The organic solubilizing agent may be any polar organic liquid having a molecular weight of less than about 250 and a Hildebrand solubility value of about 10 or higher, and mixtures thereof. Illustrative and non-limiting examples of such polar compounds (along with their Hildebrand solubility parameters) include lower alcohols, e.g., methanol (12.9), ethanol (11.2), propanol (10.2), and isopropanol (10.2), as well as nitriles, e.g., benzonitrile (10.7), acetonitrile (11.8), and propionitrile; amides, e.g., dimethylformamide (11.5), dimethylacetamide, and N,N-dimethyl-propionamide; pyrrolidones, e.g., N-methylpyrrolidone (14.8), N-methyl piperidone, 1,5-dimethyl pyrrolidone, 2-pyrrolidinone, 2-hydroxyethyl pyrrolidone, N-dodecyl pyrrolidone, N-ethyl pyrrolidone, N-cyclohexyl pyrrolidone, 1,2-di(pyrrolidone) ethane; glycols, e.g., ethylene glycol and propylene glycol; polyglycols, e.g., diethylene glycol, triethylene glycol, tetraethylene glycol, dipropylene glycol, and tripropylene glycol; sulfoxides, e.g., dimethyl sulfoxide (12.8); sulfones, e.g., dimethyl sulfone; and sulfolane. Hildebrand solubility values are an empirical measure of the relative polarity of an organic compound and are described, for example, in *Introduction to Modern~Liquid Chromatography*, by L. R. Snyder and J. J. Kirkland, pp. 215-218 (1974), a Wiley-Interscience publication, (John Wiley & Sons) and in The Solubility of Non-Electrolytes, J. H. Hildebrand and R. L. Scott, pp. 424-434, Dover Publications Inc., New York (1964). The preferred polar organic solubilizing agents are selected from amides, sulfoxides, sulfones, and mixtures thereof; the more preferred polar organic solubilizing agents being amides, for instance, N-methylpyrrolidone.

The aforementioned solubilizing liquids may be employed individually or as mixtures of two or more different polar organic liquid compounds; and the total amount of such added polar organic solubilizing agent(s) present in the non-aqueous hydroformylation reaction product composition generally corresponds to that amount employed in the reaction medium of the non-aqueous hydroformylation process from which the non-aqueous hydroformylation reaction product composition may be derived. Accordingly, the polar organic solubilizing agent(s) may be present in the non-aqueous hydroformylation reaction product composition in an amount ranging from about 10 to about 50 weight percent, preferably, from about 10 to about 30 weight percent, based on the weight of the non-aqueous hydroformylation reaction product composition.

It is to be further understood that while the separation stage is preferably directed to treating a non-aqueous hydroformylation reaction product composition that has been directly obtained by removal of a corresponding liquid reaction medium from a hydroformylation reactor, the non-aqueous hydroformylation reaction product composition may also encompass any non-aqueous hydroformylation reaction product composition derived from the hydroformylation process and pre-treated in some manner prior to the phase separation process of this invention. Of course, the pre-treated composition must be "non-aqueous," as defined herein, and must contain at least some amount of aldehyde product and the rhodium-organophosphorus ligand complex, free ligand, and the solubilizing agent for the complex and free ligand. Moreover, it is to be further understood that the amounts of each of said components in such pretreated non-aqueous composition need not necessarily be the same as those amounts of components present in the non-aqueous hydroformylation reaction product composition obtained directly from the hydroformylation process. Illustrative pre-treated non-aqueous hydroformylation reaction product compositions may include distillation residues obtained upon removing some of the aldehyde product from the non-aqueous hydroformylation reaction product composition obtained from the hydroformylation reactor; or the pretreated composition may include a liquid polar (non-aqueous) phase obtained from some other type of pre-treatment method. For instance, certain non-aqueous hydroformylation reaction product compositions obtained directly from the reactor may themselves phase separate into a polar and non-polar phase upon standing and/or when cooled to a lower temperature than the hydroformylation reaction temperature. Thus, if desired, an initial non-aqueous hydroformylation reaction product composition removed from the reactor may be subjected to any suitable pretreatment procedure in order to arrive at a pre-treated non-aqueous hydroformylation reaction product composition feed for the subject invention.

The art does not discuss the disadvantageous effects of conjugated polyolefins on the phase separation method taught in U.S. Pat. No. 5,180,854. We have now discovered that when conjugated polyolefins are present in the hydroformylation reaction product composition, the efficiency of separating and recovering rhodium via the method of U.S. Pat. No. 5,180,854 is greatly reduced. In fact, the conjugated polyolefins appear to solubilize rhodium in the aldehyde product-containing nonpolar phase resulting from the separation, possibly through formation of rhodium-$\eta^3$-allyl complexes, although such a theory should not be limiting or binding upon the invention in any manner. The solubilization of rhodium in the nonpolar phase occurs to an unacceptable extent making it difficult to achieve a rhodium concentration less than about 3 ppm by weight, based on the weight of the nonpolar phase. Such high levels of rhodium mean that rhodium is lost to the product phase, and an undesirable amount of make-up rhodium needs to be supplied to the hydroformylation process. For a description of metal-$\eta^3$-allyl complexes, refer to *Principles and Applications of Organotransition Metal Chemistry*, James P. Collman and Louis S. Hegedus, University Science Books, Mill Valley, Calif., 1980.

We have now discovered process conditions for the separation stage (or for at least one separation stage when a multiplicity of separation stages are used) that produce water soluble rhodium complexes that migrate into the polar or aqueous phase, such that rhodium can be recovered in high efficiency and recycled in a liquid catalyst recycle to the hydroformylation process. Our discovery suggests that conjugated polyolefins, which are present in the aldehyde product, may tend to form stable intermediate rhodium-$\eta^3$-allyl complexes during hydroformylation. These rhodium-$\eta^3$-allyl complexes may require greater effort to finish off the hydroformylation reaction, so as to liberate the rhodium metal for bonding into water-soluble complexes. This hypothesis is mentioned as one explanation for the advantageous effects of our discovery; but again, our hypothesis is not intended to limit the invention.

In the process of this invention, a non-aqueous hydroformylation reaction product composition is separated in one or more stages of phase separation into a polar phase containing the rhodium-organophosphorus ligand complex, the free organophosphorus ligand, the organic solubilizing agent, and added water, and a nonpolar phase containing the one or more aldehyde products, the one or more conjugated polyolefins, and optional nonpolar solvent, with improved separation and recovery of rhodium. Accordingly, the process of this invention comprises one in which water and optionally a nonpolar solvent are added to the hydroformylation reaction product composition to induce the phase separation. The amount of water added or the total amount of water and optional nonpolar solvent added to the hydroformylation reaction product composition should be sufficient to provide phase separation such that the aldehyde-containing nonpolar phase contains less than about 1.0 ppm rhodium, based on the weight of the nonpolar phase. Preferably, the added water and optional nonpolar solvent are sufficient to provide phase separation such that the aldehyde-containing nonpolar phase contains less than about 0.8 ppm (or less than 800 parts per billion, ppb), and more preferably, less than about 0.5 ppm (or 500 ppb) rhodium, based on the weight of the nonpolar phase. Preferably, the added water and optional nonpolar solvent are sufficient to provide phase separation of at least about 70 weight percent of the aldehyde product(s) and at least about 95 weight percent of the free organophosphorus ligand, calculated on the weight of the non-aqueous hydroformylation reaction product composition.

Preferably, the process of this invention comprises mixing the non-aqueous hydroformylation reaction product composition with from about 2 to about 60 percent by weight, and more preferably from about 2 to about 30 percent by weight, of added water and from 0 to about 60 percent by weight, and more preferably from about 2 to about 30 percent by weight, of an added nonpolar hydrocarbon compound, said amounts of added water and added nonpolar hydrocarbon compound being based on the total weight of the non-aqueous hydroformylation reaction product composition.

The added nonpolar hydrocarbon compound employed in this invention can be any nonpolar liquid hydrocarbon compound containing from about 6 to about 30 carbon atoms. Illustrative nonpolar hydrocarbons include, for example, alkanes containing from $C_6$ to $C_{30}$ carbon atoms having straight or branched chain structure, such as hexane, heptane, octane, nonane, decane, undecane, dodecane, tridecane, tetradecane, pentadecane, hexadecane, heptadecane octadecane, nonadecane, eicosane, docosane, tetracosane, hexacosane, and octacosane; olefinic compounds containing from $C_6$ to $C_{30}$ carbon atoms, including alpha-olefins containing from $C_6$ to $C_{30}$ carbon atoms, such as, 1-hexene and 1-octene; and cycloaliphatic compounds containing from $C_6$ to $C_{12}$ carbon atoms, such as, cyclohexane and cyclooctene. Of course, it is to be understood that such nonpolar hydrocarbon compounds may be substituted with any substituent that does not adversely affect the phase separation process of this invention. For example, illustrative substituted alkanes include fluorocarbons. Moreover, mixtures of two or more different nonpolar hydrocarbon compounds can be employed, if desired. Preferably, the nonpolar hydrocarbon is a saturated straight chain alkane containing from $C_6$ to $C_{30}$ carbon atoms, most preferably, hexane.

Removal of all or some of the non-aqueous hydroformylation liquid reaction medium from the hydroformylation reactor to obtain the corresponding non-aqueous hydroformylation reaction product composition feed to the phase separation can be accomplished in any conventional manner. In a continuous hydroformylation process, for example, a portion of the liquid hydroformylation reaction medium can be continuously pumped from the reactor to a mixer to be treated with added water or added water and an added nonpolar hydrocarbon compound, for example, by thoroughly mixing, and the treated composition phase separated into two distinct liquid layers or phases. The mixing can be carried out in any conventional manner or fashion; for example, in a static mixer or a mixer with rotating parts, or a co-current or counter-current mixer, or using spray columns, provided that the equipment is operable under the total pressure and temperature required. As used herein, the term "static mixer" means a vessel, preferably tubular in shape, with internal structures, such as perforated plates or baffles of any size or shape, which induce mixing of a liquid flowing through the vessel without moving parts, such as, a blades rotated on a shaft. Static mixers are also referred to as "In-Line" mixers. The treatment does not require any special equipment or mixing device; although a thorough mixing of the liquids is desired. Generally, it is preferred to add the water or water and nonpolar hydrocarbon compound to the non-aqueous hydroformylation reaction product composition and thoroughly mix in a static mixer, and then feed the resulting composition to any conventional decanter vessel for settling of polar and nonpolar liquid phases. If the mixing produces a fine liquid emulsion (intimately mixed small liquid droplets), then the resulting composition can be sent to a coalescer prior to the decanter vessel to obtain larger liquid droplets, which are more easily separated into two liquid phases.

The order of addition of the water, and nonpolar hydrocarbon if used, to the non-aqueous hydroformylation reaction product composition is immaterial; and they may be added separately and/or simultaneously, or premixed and then added simultaneously, if desired. Moreover, the amount of added water and amount of added nonpolar hydrocarbon is not narrowly critical and need only be that minimum amount sufficient to induce the desired phase separation. Of course, it is to be understood that the terms "added water" and "added non-polar hydrocarbon" as employed herein refer to water and nonpolar hydrocarbons that have been deliberately added to the non-aqueous hydroformylation reaction product composition feed for the purpose of the phase separation process of this invention; in contrast, for example, to non-polar hydrocarbons that might already be present in said reaction product compositions as an ancillary result of the hydroformylation reaction process itself, namely, unreacted olefin (conjugated or unconjugated), in situ produced hydrocarbons, hydrocarbons present as the result of employing impure olefin starting materials, and the like. Such amounts of ancillary type nonpolar hydrocarbons, if and when present, may lessen the amount of deliberately added non-polar hydrocarbon necessary to achieve a particular desired result of phase separation. Indeed it may be possible to deliberately add or provide for some or all of the nonpolar hydrocarbon directly in the hydroformylation reactor prior to removal of the resulting hydroformylation reaction product composition; thereby rendering it necessary to add only water, or water and a lesser amount of added non-polar hydrocarbon, to the non-aqueous hydroformylation reaction product composition feed.

The mixing treatment is conducted under process conditions that allow the hydroformylation to continue in the non-aqueous phase. Such conditions can be maintained by discharging the syn gas saturated hydroformylation reactor effluent into the mixer under pressurized conditions to prevent degassing of the dissolved carbon monoxide and hydrogen at the operating temperature. A carbon monoxide-containing gas, a hydrogen-containing gas, or a mixture thereof can also be pressurized into the mixer, if desired. Any carbon monoxide-containing gas and/or hydrogen-containing gas may be employed that is capable of producing the phase separation as required of this invention. Suitable carbon monoxide-containing gases include, without limitation, essentially pure gaseous carbon monoxide and mixtures of carbon monoxide with nitrogen, air, inert gases (Ne, Ar, K), carbon dioxide, or hydrogen (e.g., synthesis gas). Likewise, suitable hydrogen-containing gases include, without limitation, essentially pure hydrogen and mixtures of hydrogen with nitrogen, air, inert gases (Ne, Ar, K), carbon monoxide (e.g., synthesis gas), and carbon dioxide.

The partial pressure of carbon monoxide, or the partial pressure of hydrogen, or the total pressure of carbon monoxide and hydrogen required to maintain a reactive condition in the mixing operation depends upon the process conditions in the hydroformylation reactor. Typically, the total pressure in the mixer ranges from greater than about 20 psia (138 kPa) to less than about 400 psia (2,758 kPa). Preferably, the total pressure in the mixer ranges between about 20 psia (138 kPa) and about 300 psia (2,068 kPa). Pressure in the mixer may be controlled with a conventional back pressure regulator or any other suitable pressure control device. Typically, said mixing is conducted at a liquid phase temperature equal to or greater than about 50° C., and preferably, at a liquid phase temperature greater than about 50° C. and less than about 130° C. A more preferred temperature is about 75° C.+/−10° C. Residence time in the mixer ranges from about 1 minute to about 60 minutes, preferably, from about 1 minute to about 30 minutes. The feed rate of the aqueous (water) phase into the mixer typically ranges from about 10 percent to about 30 percent, and preferably about 20+/−2 percent, of the feed rate of the hydroformylation reaction product composition into the reactor, calculated in units of weight per hour.

The selection of the total pressure for the hydroformylation step and the total pressure for at least one of the separation stages (mixer) is guided by our observation that at least a minimum overall pressure is needed to achieve the effects of the invention. In this regard the "overall pressure" refers to the sum of the total pressure of the hydroformylation step and the total pressure of the separation stage containing the carbonmonoxide containing gas, the hydrogen-containing gas, or the mixture thereof. We have discovered that this overall pressure (or the aforementioned sum) should be greater than about 360 psia (2482 kPa), and preferably, greater than about 450 psia (3,103 kPa). The overall pressure (or sum) is suitably less than about 800 psia (5,515 kPa), and preferably, less than about 650 psia (4,482 kPa).

The liquid medium obtained from the mixer may optionally be forwarded to a coalescer if it is needed to convert emulsion, if any, into a larger droplet liquid medium, and from the coalescer forwarded to a decanter. Alternatively, the liquid medium from the mixer can be forwarded to the decanter directly, if no need exists for a coalescer. In the decanter, the phases separate rapidly into the nonpolar phase containing the one or more aldehydes, the one or more conjugated polyolefins, and optionally, the added nonpolar solvent, and a polar phase containing the rhodium-organophosphorus ligand complex, the free organophosphorus ligand, the organic solubilizing agent, and the added water. The decanter is typically operated at a temperature greater than 35° C., and preferably, greater than about 40° C. The decanter is typically operated at a temperature less than about 90° C. More preferably, the decanter is operated at a temperature of about 75° C.+/−10° C. Pressure in the decanter generally ranges from about 15 psia (103 kPa) to about 50 psia (345 kPa), but other pressures may be employed, if desired.

While the aldehyde-containing liquid nonpolar phase obtained from the decanter ("liquid crude nonpolar phase") need not necessarily be further purified prior to using said aldehyde, for example, in a downstream hydrogenation process, such purification if desired can be accomplished by any conventional means. Purification can remove nonpolar hydrocarbon compounds and/or polar compounds that might also be present in the nonpolar phase. For example, polar compounds may be removed from the aldehyde-containing liquid crude nonpolar phase by distillation or by employing a conventional cocurrent or counter-current liquid-liquid extractor. The latter would involve contacting the nonpolar phase obtained from the mixer/decanter containing the one or more aldehyde products, the one or more conjugated polyolefins, and the optional nonpolar solvent with a polar solvent, such as water, to recover a purified nonpolar phase containing the one or more aldehyde products, the one or more conjugated polyolefins, and the optional nonpolar solvent and a polar phase containing any residual polar compounds that were present in the liquid crude nonpolar phase. Nonpolar hydrocarbon compounds can be separated from the aldehyde products either before and/or after hydrogenation of the aldehyde product; and such recovered nonpolar hydrocarbon compounds may be recycled, if desired, as the nonpolar hydrocarbon additive to the mixer in the phase separation of the non-aqueous hydroformylation reaction product composition. It is noted that hydrogenation of the aldehyde product composition will convert the conjugated polyolefins to their corresponding saturated compounds.

The liquid-liquid extractor is typically operated at a temperature greater than about 30° C. and less than about 95° C., preferably, from about 55° C. to about 90° C. The extractor is suitably operated at a pressure ranging from about 15 psia (103 kPa) to about 20 psia (138 kPa), preferably, about 16 psia (110 kPa+/−1 psia (6.9 kPa). If desired, additional ligand may be fed to the liquid-liquid extractor to scavenge any residual rhodium. Moreover, since the nonpolar phase from the liquid-liquid extractor can be recycled to the mixer, the quantity of ligand added to the liquid-liquid extractor may supplement a similar quantity of ligand lost through degradation during non-aqueous hydroformylation.

The liquid polar phase (aqueous phase) obtained from the mixer/decanter, containing the rhodium-organophosphorus ligand complex, the free organophosphorus ligand, the organic solubilizing agent, and the added water may be treated to remove the water by any conventional method, such as by pumping the aqueous polar phase to any conventional vaporizer-separator. The resulting non-aqueous polar phase containing the rhodium-organophosphorus ligand complex, the free organophosphorus ligand, and the solubilizing agent is preferably recycled back to the hydroformylation reactor of the non-aqueous hydroformylation reaction process in order to achieve a continuous, liquid catalyst recycle. If desired, two or more vaporizer-separators may be employed so that the aqueous separation process is repeated. For example, the non-aqueous polar phase obtained from the bottoms of the first vaporizer can be employed as the feed to the second vaporizer-separator; and the bottoms from the second vaporizer can be recycled to the hydroformylation reactor. The aqueous overhead accumulated from the first and/or second vaporizers, consisting essentially of water, can be recycled back to the mixer or the extractor.

In addition, all or a portion of the aqueous polar solution obtained from the liquid-liquid extractor discussed above may have its water removed by conveying in analogous fashion the aqueous polar solution to a distillation column, and the resulting non-aqueous polar solution may also be returned to the hydroformylation reactor. A purified water obtained from the distillation may be returned to said liquid-liquid extractor. For efficiency purposes and in order to avoid undue aqueous wetting of the rhodium-organophosphorus ligand complex in the liquid polar aqueous phase obtained from the mixer-decanter, it may be preferred to employ a different vaporizer-separator if water is to be removed from any additional liquid polar solution obtained from the liquid-liquid extractor.

Thus, as described above, the subject invention may be further depicted by referring to the FIGURE of the drawing wherein syn gas (CO and $H_2$) and a mixture of olefinically-mono-unsaturated and olefinically-poly-unsaturated compounds (preferably, a mixture of mono- and poly-unsaturated fatty acid esters) are fed through lines 1 and 2, respectively, into a hydroformylation zone 101 (alternatively, referred to as an OXO reactor), which contains the rhodium-organophosphorus ligand complex catalyst, free organophosphorus ligand, and the polar organic solubilizing agent for said complex and said free ligand, and wherein the non-aqueous hydroformylation of the olefinic compounds takes place, preferably, to a conversion of greater than about 50 percent and less than 100 percent of all unsaturated bonds, such that the product mixture further comprises, in addition to the aforementioned components, one or more aldehyde products and one or more conjugated poly-unsaturated fatty acid ester(s) (conjugated polyolefins). All or a portion of the corresponding liquid aldehyde containing non-aqueous hydroformylation reaction product medium is then continuously withdrawn from the hydroformylation zone 101 to provide the non-aqueous hydroformylation reaction product composition fed into the phase separation system, comprising a mixer (102), decanter (103), liquid-liquid extractor (104), and various distillation columns (105, 106), via line 4. Water and/or water and a non-polar hydrocarbon are then added to said withdrawn reaction product composition via lines 3 and 12, and thoroughly mixed therewith, in mixer 102, preferably, a static mixer. Gas composition and pressure in the mixer can be regulated via gas line 16. The resultant aqueous composition is conveyed via line 4a to a liquid decanter vessel 103, wherein said treated composition settles into two distinct liquid phases, that is, a non-polar phase comprising the desired aldehyde product(s), unconverted conjugated polyolefin(s), any other unconverted olefin(s), and the non-polar hydrocarbon additive of line 3 when employed, and a liquid polar phase comprising the rhodium-organophosphorus ligand complex, free organophosphorus ligand, the polar organic solubilizing agent for said complex and said free ligand, and the added water. The liquid aldehyde containing non-polar phase may be removed from the decanter vessel 103 via line 5 and conveyed to a liquid-liquid extractor 104. Polar compounds that might also be present in the liquid aldehyde-containing nonpolar phase may be removed therefrom with the aid of water (and a rhodium scavenger if desired, such as, a corresponding monosulfonated tertiary phosphine metal salt ligand via line 15 and then into line 13, in the amount preferably not to exceed what is lost through ligand degradation in the hydroformylation process) added to said liquid-liquid extractor 104 via line 13; and the desired purified liquid aldehyde product may be obtained and recovered from said extractor via line 9. Said aldehyde product so obtained may contain additional non-polar hydrocarbon compounds, such as, unreacted olefin and the non-polar hydrocarbon additive, when employed, and may be further purified, if desired, in any conventional manner not shown, e.g., by distillation or additional extraction. The aqueous liquid polar phase in said decanter 103, containing the rhodium-organophosphorus ligand complex and free ligand, may be removed therefrom via line 6 and conveyed to a vaporizer/separator 105 for removal of the water; and the non-aqueous composition obtained therefrom, containing rhodium-organophosphorus ligand complex and free organophosphorus ligand, may be recycled to the hydroformylation reactor via line 8. The water recovered from said vaporizer/separator 105 can be recycled to the mixer 102 via line 7. Moreover, all or a portion of the aqueous composition obtained from said liquid-liquid extractor 104 via line 10 may be conveyed via line 12 into line 4 containing the non-aqueous hydroformylation reaction product composition for input to the mixer; or alternatively, all or a portion of said aqueous composition from line 10 may be conveyed via line 11 to a distillation column 106, wherein the water may be separated from any of the other polar compounds that may be present, such as, the polar organic solubilizing agent. In general, it is preferred to divide the aqueous composition of said line 10 into two streams, one stream serving as the source of said line 12 and the other as the source of said line 11. The purified water from said distillation column 106 may be reused and returned to said liquid-liquid extractor 104 via line 13, while the polar compounds such as the polar organic solubilizing agent obtained from said distillation column 106 may be recycled to the hydroformylation reactor 101 via line 14.

Other embodiments of the FIGURE may be found further disclosed herein and/or will be obvious to one skilled in the art. For instance, the source of water added to the non-aqueous hydroformylation reaction product composition via line 12 need not be derived from the aqueous composition of line 10, but could be obtained from a different supply of water from line 13 or some other source not shown. The same is also true of water added to extractor 104 via line 13; it also could be obtained from a supply of water not shown. For example, obviously an initial supply of water is needed at the start up of the process and such may be accomplished by adding said water to line 12 or line 13, or in any other appropriate manner not shown. Moreover, if desired all or part of the aqueous composition of line 10 could first go to vaporizer/separator not shown; the water and vaporized materials collected therefrom going to distillation column 106 and tails from the vaporizer going to vaporizer/separator 105 or some other vaporizer/separator, not shown.

The following examples are illustrative of the present invention and are not to be regarded as limiting thereof. It is to be understood that all parts, percentages and proportions referred to herein and in the appended claims are by weight unless otherwise indicated.

EXAMPLES 1A-1F

With reference to the FIGURE, a catalyst solution was prepared in a glove box under nitrogen by dissolving rhodium (dicarbonyl)acetylacetonate [$Rh(CO)_2(acac)$] (6.03 g) and dicyclohexylphenylphosphine monosulfonate sodium salt ($DCHPPMS^-Na^+$) (110.05 g) in 1-methyl-2-pyrrolidinone (NMP, 698.3 g). The catalyst solution was purged with and maintained under nitrogen gas. The catalyst solution was charged into three stirred-tank reactors connected in series in the following amounts: Reactor A, 343.4 g; Reactor B, 272.1 g; and Reactor C, 191.7 g. The charge was made under nitrogen, and then the nitrogen was purged out of the reactors with synthesis gas. The reactors were then pressurized with synthesis gas (1:1 mixture of hydrogen and carbon monoxide) to a total gas pressure as follows: 424 psia (2.92 MPa), 414 psia (2.86 MPa), and 404 psia (2.79 MPa) for Reactors A, B, and C, respectively. A soy methyl ester feed comprising 26 weight percent mono-unsaturated fatty acid esters, 52 weight percent di-unsaturated fatty acid esters, 7 weight percent tri-unsaturated fatty acid esters, and 15 weight percent saturated fatty acid esters was pumped into each reactor in the following amounts: Reactor A, 627 g; Reactor B, 680 g; and Reactor C, 739 g. The reaction solution was heated to 75° C. and stirred at the following stirring rates: Reactor A, 616 revolutions per minute (rpm); Reactor B, 595 rpm; Reactor C, 470 rpm. When the desired conversion (about 67% of the double bonds) was achieved, a fresh soy methyl ester feed of the same composition as noted above was fed into Reactor A at a rate of 400 g/hour. Simultaneously, a flow was initiated of reaction solution from Reactor A to Reactor B, and from Reactor B to Reactor C; as well as feeding effluent from the Reactor C into a static mixer (FIGURE, unit 102) via line 4. Water was introduced via line 10 into line 12 at about 80 g/hour to be mixed with the hydroformylation reaction effluent from Reactor C. An aqueous composition resulting from combining the hydroformylation reactor effluent and water in line 4 was forced into the static mixer by the pressure in the reactor, and the pressure in the mixer was maintained by a back pressure regulator via line 16. The total pressure in the static mixer was initially set by a back pressure regulator at 250 psig (1,724 kPa). The temperature of the static mixer was initially set at 75° C. The overall total pressure of the hydroformylation reactor and the static mixer was initially set at 650 psia.

The discharge from the static mixer, a nearly emulsified liquid, was passed through a coalescer in order to obtain larger droplets, from whence the discharge was further forwarded to a decanter, (FIGURE, unit 103) for settling of the aqueous and non-aqueous phases. The decanter was maintained at 45° C. and 2.5 psia (17 kPa). The top phase of the decanter, which comprised the non-aqueous phase, was fed into the bottom of an extractor (FIGURE, unit 104) at a rate of about 424 g/hour. Water was fed at a rate of 80 g/hour into the top of the extractor. An aldehyde-containing product was withdrawn from the top of the extractor at a rate of 440 g/hour. The bottom phase from the decanter, containing the rhodium-organophosphorus ligand complex, free organophosphorus ligand, NMP, and added water, was mixed with make-up NMP, which was fed at 60 g/h and adjusted as needed to balance the NMP stripping rate; and thereafter the resulting phase was fed to a vaporizer (FIGURE, unit 105) to remove water so as to recover a liquid non-aqueous catalyst solution containing the rhodium-organophosphorus ligand complex, the free organophosphorus ligand, and NMP. The liquid catalyst solution was recycled to Reactor A. When the continuous reaction system reached a steady state, samples were collected and analyzed to obtain the olefin conversion, product composition, and concentrations of ligand, rhodium metal, and NMP in the reactors as well as the various liquid phases of the mixer, decanter, and extractor. As used herein, the term "steady state" refers to a process state characterized by essentially steady liquid flow rates in the system and essentially steady compositions in each reactor (within +/−10 percent), as determined by gas chromatography analysis. Typically, a "steady state" is reached in about 24 to about 48 hours after start-up of the process. The experiment was conducted over a period of 1800 hours, during which time the reaction and phase separation process conditions were varied to investigate the effects of synthesis gas pressure and temperature in the various reactor and separation units on the efficiency of rhodium separation. In each example, the overall pressure, or the sum of the total pressure in the hydroformylation stage and the total pressure in the static mixer, was greater than 360 psia (2482 kPa). The results of these experiments are shown in Table 1.

TABLE 1

| Expt. | 1-A | 1-B | 1-C | CE-1 | 1-D | 1-E | 1-F |
|---|---|---|---|---|---|---|---|
| Reaction Time (h) | 115 | 211 | 354 | 528 | 757 | 1005 | 1384 |
| Reactor Total Pressure (psia) | 400 | 400 | 400 | 300 | 300 | 300 | 300 |
| Mixer Temp (° C.) | 75 | 75 | 77 | 77 | 75 | 75 | 60 |
| Mixer Total Pressure, psia | 250 | 100 | 20 | 20 | 100 | 200 | 200 |
| Overall Pressure $P_{Reactor} + P_{Mixer}$ | 650 | 500 | 420 | 320 | 400 | 500 | 500 |
| Rh in Product, ppbw | 150 | 240 | 460 | 1800 | 750 | 370 | 420 |

Comparative Experiment CE-1

For comparative purposes, the hydroformylation and phase separation process was conducted in a manner similar to that described in Examples 1-D and 1-E, with the exception that the mixer pressure was lowered to 20 psia. The mixer temperature in this comparative experiment was only 2 degrees higher than in examples 1-D and 1-E. Results are shown in Table 1. When this comparative experiment is compared with examples 1-D and 1-E, it is seen that an increase in the overall pressure from 320 psia to 400 psia substantially decreased the quantity of rhodium retained in the non-polar aldehyde product-containing phase.

What is claimed is:

1. A non-aqueous hydroformylation process with a separation stage for recovery of aldehyde product(s) and recovery of rhodium catalyst, the process comprising:
   (a) hydroformylating a mixture of olefinically-mono-unsaturated and olefinically-poly-unsaturated compounds with carbon monoxide and hydrogen in the presence of a rhodium-organophosphorus ligand complex, a free organophosphorus ligand, and a polar organic solubilizing agent for said complex and said free ligand, in a hydroformylation reactor at a total pressure ranging from 250 psia (1,724 kPa) to 450 psia (3,103 kPa); and obtaining therefrom a non-aqueous hydroformylation reaction product composition comprising one or more aldehyde products, one or more conjugated polyolefins, the rhodium-organophosphorus ligand complex, the free organophosphorus ligand, and the polar organic solubilizing agent for said complex and said free ligand; wherein the one or more aldehyde products each comprise greater than 8 carbon atoms; wherein the one or more olefinically-mono-unsaturated compounds, one or more olefinically poly-unsaturated compounds, and one or more conjugated poly-olefins each comprise greater than 7 carbon atoms; and the organophosphorus ligand comprises an ionically-charged organophosphine ligand; and
   (b) separating said hydroformylation reaction product composition by contacting said composition with water and optionally a nonpolar solvent under conditions sufficient to obtain by one or more stages of phase separation a nonpolar phase comprising the one or more aldehyde products, the one or more conjugated polyolefins, the optional nonpolar solvent, and rhodium in a concentration less than 1.0 ppm by weight, based on the weight of the nonpolar phase, and a polar phase comprising the rhodium-organophosphorus ligand complex, the free organophosphorus ligand, the polar organic solubilizing agent, and added water; the contacting with water and optional nonpolar solvent in at least one stage of phase separation occurring in the presence of a carbon monoxide-containing gas, a hydrogen-containing gas, or a mixture thereof at a total pressure greater than 20 psia (138 kPa) and less than 400 psia (2,758 kPa); provided that the sum of the total pressure in the hydroformylation step (a) and the total pressure of the at least one separation step (b) in employing said aforementioned gas is greater than 360 psia (2,482 kPa).

2. The process of claim 1 further comprising a step (c) of removing the added water from the polar phase and recycling said resulting polar non-aqueous phase comprising the rhodium-organophosphorus ligand complex, the free organophosphorus ligand, and the polar organic solubilizing agent back to the hydroformylation step (a).

3. The process of claim 1 wherein the process is conducted in a continuous manner of operation.

4. The process of claim 1 wherein the hydroformylation step (a) is conducted at a temperature greater than 40° C. and less than 130° C.

5. The process of claim 1 wherein the hydroformylation step (a) is conducted at a rhodium concentration ranging from 10 ppm to 800 ppm, calculated as rhodium metal and based on the weight of the non-aqueous hydroformylation reaction product composition.

6. The process of claim 1 wherein the hydroformylation step (a) is conducted with an amount of organophosphorus ligand ranging from 0.2 to 4.0 weight percent, based on the weight of the non-aqueous hydroformylation reaction product composition.

7. The process of claim 1 wherein at least one stage of separation step (b) is conducted in a mixer in the presence of a carbon monoxide-containing gas or synthesis gas; and optionally, the mixer is a static mixer.

8. The process of claim 7 wherein the separation step (b) is conducted at a temperature equal to or greater than 50° C. and less than 130° C.

9. The process of claim 7 wherein a liquid medium obtained from the mixer of separation step (b) is forwarded to a decanter to obtain therefrom the nonpolar phase comprising the one or more aldehyde products, the one or more conjugated polyolefins, and optionally, the nonpolar solvent and the polar phase comprising the rhodium-organophosphorus ligand complex, the free organophosphorus ligand, the polar organic solubilizing agent, and the added water.

10. The process of claim 9 wherein the decanter is operated at a temperature greater than 35° C. and less than 90° C. and at a pressure from 15 psia (103 kPa) to 50 psia (345 kPa).

11. The process of claim 9 wherein the nonpolar liquid phase obtained from the decanter is forwarded to a liquid-liquid extractor and mixed with added water for separation and recovery of the aldehyde product(s) containing less than 800 parts per billion rhodium.

12. The process of claim 11 wherein the liquid-liquid extractor is operated at a temperature greater than 30° C. and less than 95° C. and at a pressure ranging from 15 psia (103 kPa) to 20 psia (138 kPa).

13. The process of claim 11 wherein a polar phase is obtained from the liquid-liquid extractor comprising the rhodium-organophosphorus ligand complex, the free organophosphorus ligand, the polar organic solubilizing agent, and the added water.

14. The process of claim 13 wherein the polar phase is treated to remove the water; and a resulting non-aqueous polar phase comprising the rhodium-organophosphorus ligand complex, the free organophosphorus ligand, and the polar organic solubilizing agent is recycled to the hydroformylation step (a); and the water recovered is recycled to the mixer and/or the liquid-liquid extractor.

15. The process of claim 11 wherein a non-polar phase is obtained from the liquid-liquid extractor comprising the one or more aldehyde products, the one or more conjugated polyolefins, and optionally, the nonpolar solvent; and such nonpolar phase is purified by distillation or liquid-liquid extraction to recover the one or more aldehyde products.

16. The process of claim 1 wherein the mixture of olefinically-mono-unsaturated and olefinically-poly-unsaturated compounds comprises a mixture of one or more mono-unsaturated fatty acid esters and one or more poly-unsaturated fatty acid esters.

17. The process of claim 16 wherein the mixture of mono-unsaturated fatty acid esters and poly-unsaturated fatty acid esters is derived from the transesterification of a seed oil with a $C_{1-8}$ alkanol.

18. The process of claim 1 wherein the mixture of olefinically-mono-unsaturated and olefinically-poly-unsaturated compounds comprises a mixture of mono-unsaturated and poly-unsaturated fatty acid esters derived from a seed oil; the organophosphorus ligand comprises an ionically-charged organophosphine ligand represented by the following formula:

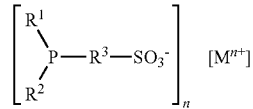

wherein $R^1$ and $R^2$ each individually represent a radical containing from 1 to 30 carbon atoms selected from the group consisting of alkyl, aryl, alkaryl, aralkyl and alicyclic radicals; wherein $R^3$ represents a divalent alkylene radical having from 2 to 12 carbon atoms, or a divalent 1,3-phenylene radical; wherein M represents a metal cation selected from the group consisting of alkali and alkaline earth metals; and wherein n has a value of 1 or 2 corresponding to the valence of the particular metal cation represented by M.

19. The process of claim 18 wherein the organophosphorus ligand comprises an ionically-charged organophosphine ligand represented by the following formula:

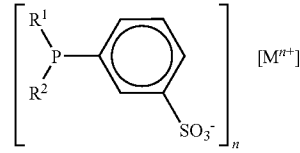

wherein $R^1$ and $R^2$ each individually represent a radical containing from 1 to 30 carbon atoms selected from the group consisting of alkyl, aryl, alkaryl, aralkyl and alicyclic radicals; wherein M represents a metal cation selected from the group consisting of alkali and alkaline earth metals; and wherein n has a value of 1 or 2 corresponding to the valance of the particular metal cation represented by M; wherein the hydroformylation process is conducted at a temperature greater than 50° C. and less than 130° C. and at a pressure greater than 275 psia (1,896 kPa) and less than 450 psia (3,1103 kPa); wherein in step (b) a static mixer is employed at a temperature of 75° C.+/−10° C. under a carbon monoxide-containing gas at a pressure greater than 20 psia (138 kPa) to 300 psia (2,068 kPa); and wherein an effluent from the static mixer is forwarded to a decanter; and a liquid non-aqueous phase obtained from the decanter is forwarded to a liquid-liquid extractor for separation and recovery of one or more aldehyde products.

20. The process of claim 1 wherein the nonpolar phase containing the aldehyde product(s) contains less than 800 parts per billion rhodium.

21. The process of claim 1 wherein the phase separation step (b) provides for separation of at least 70 weight percent of the aldehyde product(s) from the hydroformylation reaction product composition.

22. The process of claim 1 wherein the phase separation step (b) provides for separation of at least 95 weight percent of the free organophosphorus ligand from the hydroformylation reaction product composition.

23. The process of claim 1 wherein the ionically-charged organophosphine ligand is represented by the following formula:

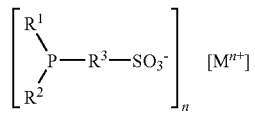

wherein $R^1$ and $R^2$ each individually represent a radical containing from 1 to 30 carbon atoms selected from the group consisting of alkyl, aryl, alkaryl, aralkyl and alicyclic radicals; wherein $R^3$ represents a divalent alkylene radical having from 2 to 12 carbon atoms, or a divalent 1,3-phenylene radical; wherein M represents a metal cation selected from the group consisting of alkali and alkaline earth metals; and wherein n has a value of 1 or 2 corresponding to the valence of the particular metal cation represented by M.

* * * * *